US00PP29266P2

(12) United States Plant Patent
Reeves

(10) Patent No.: US PP29,266 P2
(45) Date of Patent: May 1, 2018

(54) JAPANESE BLUEBERRY PLANT NAMED 'TSF 001'

(50) Latin Name: *Elaeocarpus decipiens*
Varietal Denomination: TSF 001

(71) Applicant: TreeSap Farms, LLC, Houston, TX (US)

(72) Inventor: Anthony Brent Reeves, Folsom, LA (US)

(73) Assignee: TreeSap Farms, LLC, Houston, TX (US)

( * ) Notice: Subject to any disclaimer, the term of this patent is extended or adjusted under 35 U.S.C. 154(b) by 0 days. days.

(21) Appl. No.: 15/330,567

(22) Filed: Oct. 11, 2016

(51) Int. Cl.
*A01H 5/00* (2018.01)

(52) U.S. Cl.
USPC ..... Plt./226

(58) Field of Classification Search
USPC ..... Plt./226, 216, 373
CPC ..... A01H 5/00; A01H 5/02
See application file for complete search history.

(56) References Cited

U.S. PATENT DOCUMENTS

PP17,611 P2 * 4/2007 Proud ..... A01H 5/02
Plt./226

OTHER PUBLICATIONS

Ritter. Striving for Diversity: Japanese Blueberry Tree, Pacific Horticulture Society 2011 retrieved on Sep. 27, 2017, retrieved from the Internet at http://www.pacifichorticulture.org/articles/striving-for-diversity-japanese-blueberry-tree/ 11 pp. (Year: 2011).*

* cited by examiner

*Primary Examiner* — June Hwu
(74) *Attorney, Agent, or Firm* — Klarquist Sparkman, LLP

(57) ABSTRACT

A new and distinct cultivar of *Elaeocarpus* plant named 'TSF 001', characterized by glossy red new growth and stems, vigorous growth, and ease of asexual propagation.

5 Drawing Sheets

Latin name of the genus and species of the plant claimed: *Elaeocarpus decipiens.*

Variety denomination: 'TSF 001'.

BACKGROUND OF THE INVENTION

The present invention comprises a new and distinct cultivar of *Elaeocarpus decipiens*, and hereinafter referred to by the cultivar name 'TSF 001'.

The new Japanese blueberry tree 'TSF 001' was discovered in Glen Flora, Tex. in May 2014 growing among a group of 500 15 gallon seedlings of *Elaeocarpus decipiens* in a nursery production environment. The seedlings that the new *Elaeocarpus decipiens* was made from ranged in height from 3-4 feet with a spread of 1.5-3 feet in a nursery production environment. These seedlings were produced from seeds from open pollination trees of *Elaeocarpus decipiens.*

BRIEF SUMMARY OF THE INVENTION

The 'TSF 001' variety is distinguished from other Japanese blueberry tree varieties due to the following unique combination of characteristics: grayish red new foliage (RHS-178A) and dark red (RHS-183B) to light olive brown (RHS 199B) stems, vigorous growth, and ease of asexual propagation, compared to typical Japanese blueberry trees germinated from seed.

Asexual reproduction of the new cultivar 'TSF 001' was first performed in Glen Flora, Tex. by cuttings. Through asexual reproduction of this new variety by both terminal and sub terminal cuttings, multiple generations have been reproduced, which have shown that the unique features of this cultivar are stable and reproduced true to type.

The following detailed description concerns the original plant 'TSF 001'. The original plant and progeny have been observed growing in a cultivated area in Glen Flora, Tex. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart, six edition, 2015.

BRIEF DESCRIPTION OF THE DRAWINGS

All of the images in the figures were obtained in September 2016. The 'TSF 001' plant shown was approximately 2.5 years old from a seedling was grown outdoors in a commercial nursery in a container in Glen Flora, Tex.

The colors of an illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'TSF 001' variety is based on observations of plants from initial lot of cuttings. These original cuttings produced 15 gallon Japanese blueberry tree which are two years of age and growing in Glen Flora, Tex. During the production of the plants, day temperatures ranged from about 4° C. to about 37° C. and night temperatures ranged from about −3° C. to about 25° C.

Parentage:

*Female parent*.—Unnamed selection of *Elaeocarpus decipiens*, not patented.

*Male parent*.—Unnamed selection of *Elaeocarpus decipiens*, not patented.

Figure 1:
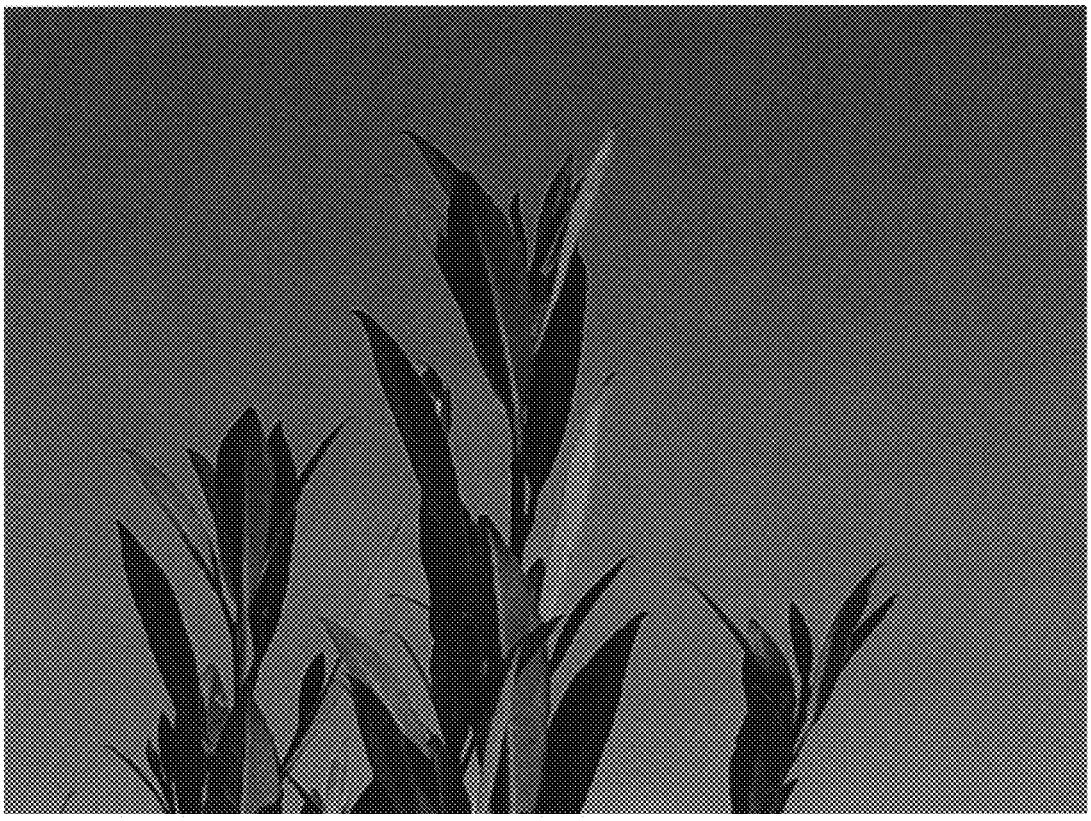
FIG. 1 illustrates maroon new growth of a 'TSF 001' plant grown outdoors in a commercial nursery in a container in Glen Flora, Tex.
Figure 2:
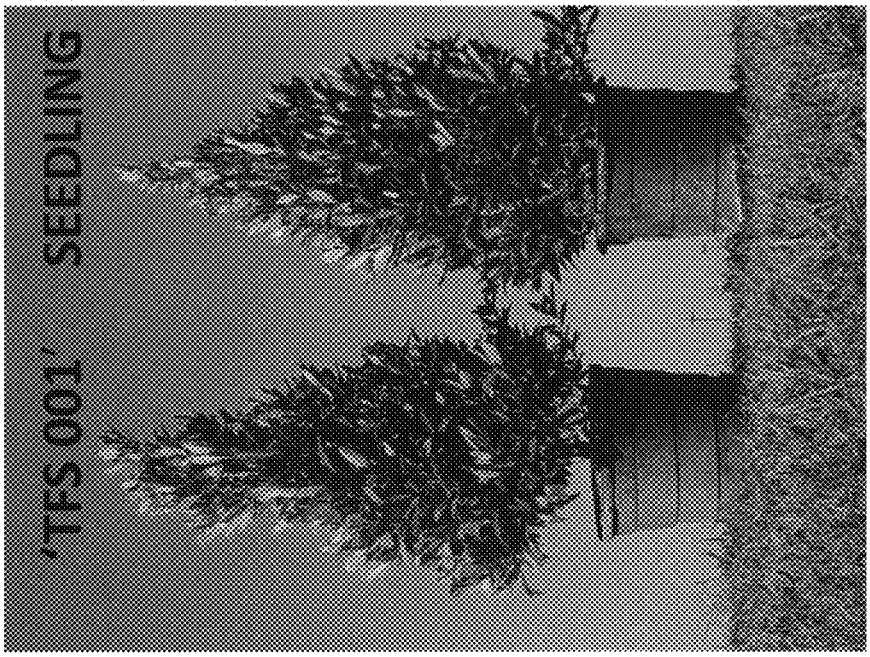
FIG. 2 illustrates a comparison of a 'TSF 001' plant and a typical Japanese blueberry seedling grown outdoors in a commercial nursery in a container in Glen Flora, Tex.
Figure 3:
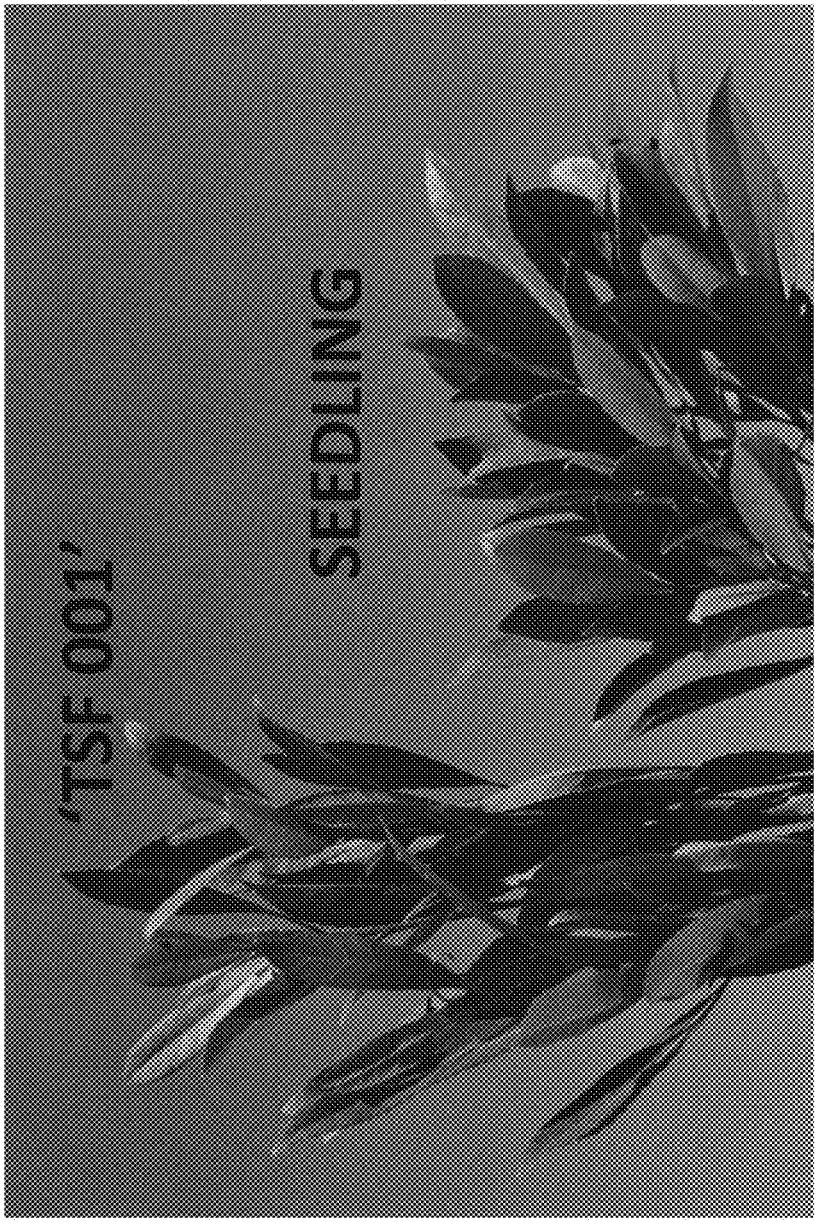
FIG. 3 illustrates a comparison of the new growth of a 'TSF 001' plant and a typical Japanese blueberry seedling grown outdoors in a commercial nursery in a container in Glen Flora, Tex. Note the newly emerging leaves of a typical seedling Japanese blueberry leaves are moderate yellow green (RHS-146B), while the upper leaf surface on newly emerging leaves of 'TSF 001' are grayish red (RHS-178A).
Figure 4:
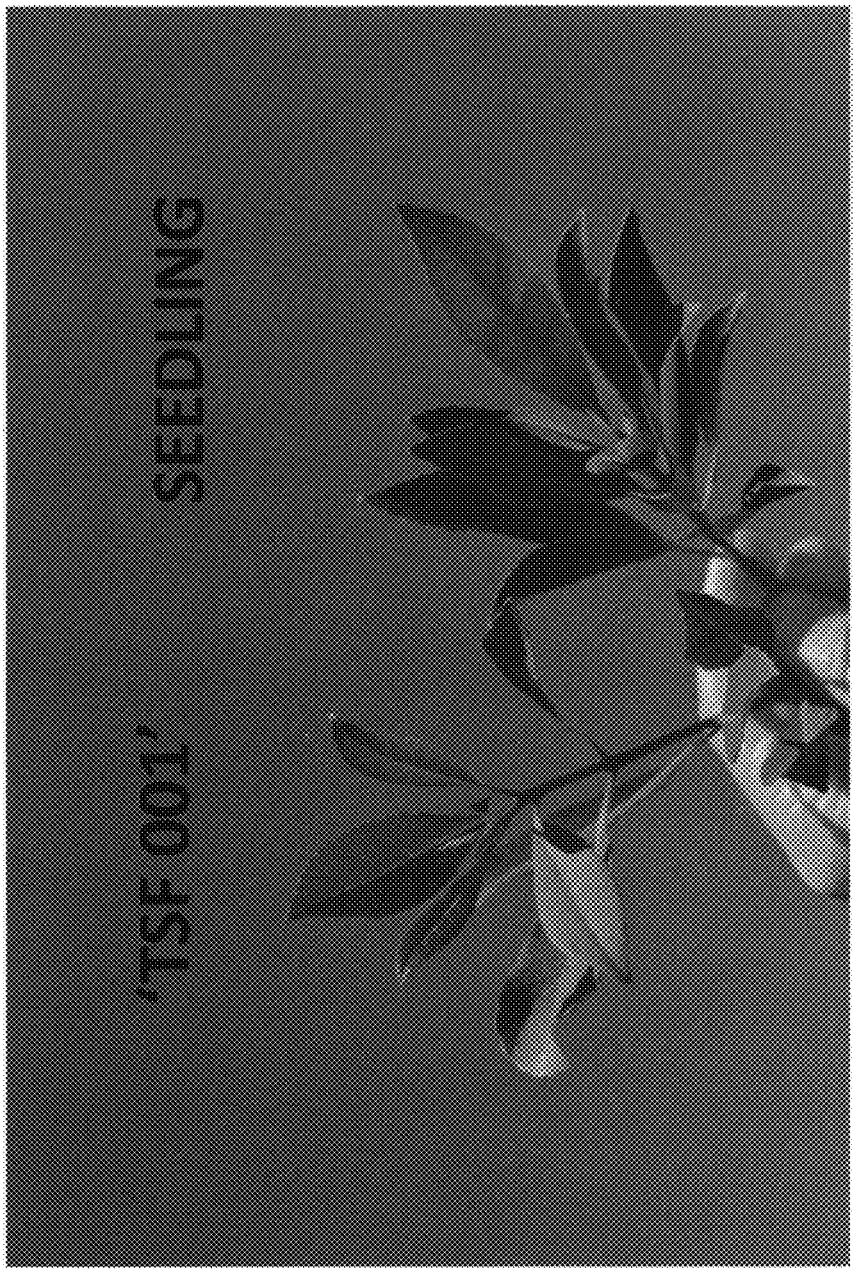
FIG. 4 illustrates a comparison of the stems of a 'TSF 001' plant and a typical Japanese blueberry seedling grown outdoors in a commercial nursery in a container in Glen Flora, Tex. Note the maroon stem observed with 'TSF 001', which is not observed on the typical Japanese blueberry seedling.

Parent comparison: Other *Elaeocarpus* cultivars are not readily available for comparison. Plants of the new cultivar 'TSF 001' are considered evergreen (see FIG. 2) and differ from typical Japanese blueberry seedlings by their maroon new leaves and stems (see FIGS. 3-4) as well as a faster growth rate. For example, the leaf color on the upper leaf surface of newly emerging leaves of a typical seedling Japanese blueberry leaves are moderate yellow green (RHS-146B), while the upper leaf surface on newly emerging leaves of 'TSF 001' are grayish red (RHS-178A). As time passes, the leaf color changes to moderate olive green (RHS-146B) on both typical Japanese blueberry plants and on 'TSF 001'.

Figure 5:
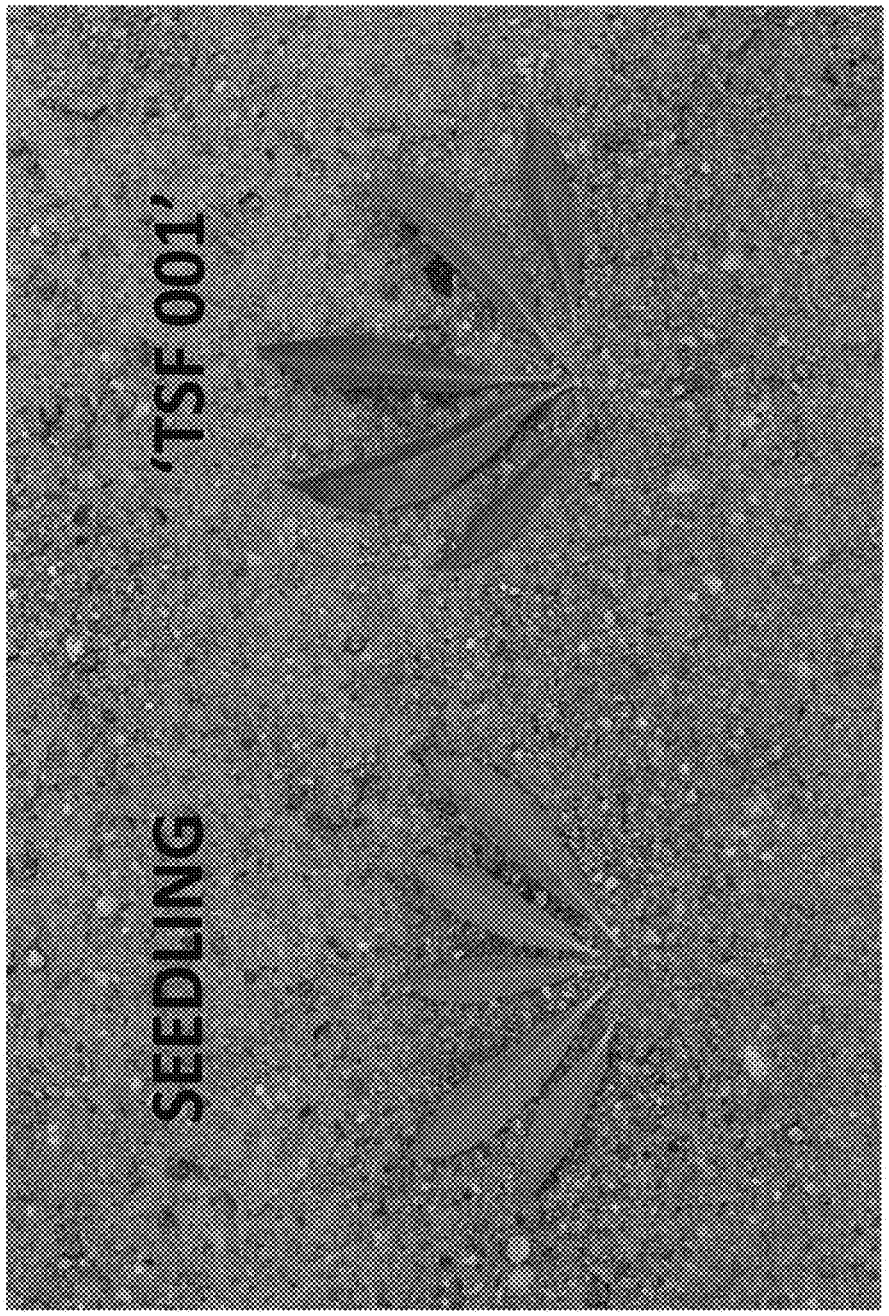
FIG. 5 illustrates a comparison of the leaf senescence of a 'TSF 001' plant and a typical Japanese blueberry seedling grown outdoors in a commercial nursery in a container in Glen Flora, Tex. Note the vivid red (RHS-45A) color observed with 'TSF 001' versus vivid reddish orange (RHS-32A) color for a typical Japanese blueberry seedling.

Commercial comparison: Plants of the new cultivar 'TSF 001' are faster growing than typical seedlings. Data collected on 15 gallon plants in Glen Flora, Tex. in July & September of 2016 showed that 'TSF 001' grew 21% and 18% faster, respectively, when compared to typical seedlings. Secondly, the color of the new growth of 'TSF 001' has a distinct maroon color, compared to a more olive green new growth on typical seedlings. Furthermore, during leaf senescence the distinct maroon leaf attributes come back. Just prior to leaf senescence, 'TSF 001' exhibits vivid red (RHS-45A) leaves compared to typical seedlings which are vivid reddish orange (RHS-32A) (see FIG. 5).

Propagation:

*Time of year*.—Late September-Early October.

*Type*.—Terminal & sub terminal cuttings.

*Size cutting*.—10 cm-15 cm.

*Wounding*.—None needed.

*Hormone*.—4000 ppm IBA+500 ppm NAA.

*Time to produce a rooted young plant*.—21 days for root initiation.

*Typical rooting percentage*.—85% with 'TSF 001', where as other *Elaeocarpus decipiens* progeny ranges from 65%-70%.

*Root description*.—Coarse, blount.

*Rooting habit*.—Medium aggressive, laterial.

Plant description: Plants used in the photographs and for this botanical description were grown in 15 gallon plastic containers for 15 months, in a full sun environment, at our production facility in Glen Flora, Tex.

*Form*.—Woody small tree, produced upright and columnar.

*Plant height*.—140 cm.

*Plant diameter*.—76 cm.

*Lateral branches*.—Length: 50.8 cm. Diameter: 4.1 cm. Internode length: 0.5-2.55 cm. Strength: Pliable but strong. Texture: Smooth. Color, young: Dark Red (RHS-183B). Color, woody: Light Olive Brown (RHS-199B).

*Foliage description*.—Arrangement: Alternate; simple. Length: 11.7 cm. Width: 3.06 cm. Shape: Elliptical. Aspect: Flat. Apex: Acute. Base: Cuneate. Margin: Serrate. Texture, upper and lower surfaces: Smooth, glabrous. Venation pattern: Pinnate. Color: Developing foliage, upper surface and lower surface is the same — Grayish Red (RHS-178A). Fully expanded foliage, upper surface — Moderate Olive Green (RHS-147A) and lower surface — Moderate Yellow Green (RHS-147B). Venation, upper surface: Strong Yellow Green (RHS-143B). Venation, lower surface mid rib: Moderate Red (RHS-184B). lateral veins, Moderate Yellow Green (RHS-147C). Petiole length: About 1.4 cm. Petiole diameter: 2 mm. Petiole texture, upper and lower surfaces: Slight pubescences. Petiole color, upper surface: Dark Red (RHS-183B). Petiole color, lower surface: Moderate Brown (RHS-165A).

Flower description: Flower development has not been observed to date.

Fruit/seed production: Fruit and seed development have not been observed to date.

Disease, pest, and stress resistance: N/A.

Temperature tolerance: Tolerant to a low temperature of −3° C. and a high temperature about 39° C.

I claim:

1. A new and distinct cultivar of *Elaeocarpus* plant, substantially as herein shown and described.

* * * * *